US006485972B1

(12) United States Patent
McMahon et al.

(10) Patent No.: US 6,485,972 B1
(45) Date of Patent: Nov. 26, 2002

(54) WNT SIGNALLING IN REPRODUCTIVE ORGANS

(75) Inventors: Andrew P. McMahon, Lexington, MA (US); Brian A. Parr, Boulder, CO (US); Seppo Vaino, Oulu (FI)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/417,039

(22) Filed: Oct. 12, 1999

Related U.S. Application Data

(60) Provisional application No. 60/104,355, filed on Oct. 15, 1998.

(51) Int. Cl.[7] .............................. C12N 5/00; C12N 1/04; A61P 15/00; C07K 1/00; C07H 21/04
(52) U.S. Cl. ........................ 435/374; 435/6; 435/7.2; 435/7.21; 435/69.5; 435/260; 530/350; 436/501; 514/2; 514/44; 536/23.5; 424/2
(58) Field of Search .................. 514/2, 44; 536/23.5; 530/350; 435/6, 7.21, 7.2, 69.1, 374, 260; 436/501; 424/2

(56) References Cited

U.S. PATENT DOCUMENTS

| | | | | |
|---|---|---|---|---|
| 3,992,520 | A | 11/1976 | Gwatkin .................. | 424/85 |
| 5,387,611 | A | 2/1995 | Rubinstein ................ | 514/588 |
| 5,563,059 | A | 10/1996 | Alak et al. ............... | 435/240.2 |
| 5,583,128 | A | 12/1996 | Bhatnagar ................ | 514/177 |
| 5,641,487 | A | 6/1997 | Dean ....................... | 424/184.1 |
| 5,756,115 | A | 5/1998 | Moo-Young et al. ....... | 424/425 |
| 5,762,956 | A | 6/1998 | Chien et al. .............. | 424/449 |

FOREIGN PATENT DOCUMENTS

| | | | | |
|---|---|---|---|---|
| WO | WO 90/02809 | 3/1990 | ............ | C12P/21/00 |
| WO | WO 92/09690 | 6/1992 | ............ | C12N/15/00 |

OTHER PUBLICATIONS

Vaino et al., Nature 397 c405–409) 1999.*
Ku and Melton, Development 119:1161–1173, 1993.*
Gazit et al., Oncogene 18:5959–5966 ,1999.*
Anzaldua et al, Differential effects of 5α–Norethisterone on the Histomorphology of the Oviduct and Uterus of the Pregnant Rabbit, 1998, Contraception 57:349–55.
Ashok et al., 1998, Lancet 352:542–543.
Barbas et al., Semisynthetic combinatorial antibody libraries: A chemical solution to the diversity problem, 1992 PNAS 89:4457.
Behringer et al., Mullerian–Inhibiting Substance Function during Mammalian Sexual Development, Cell, 1994, vol. 79, p. 415–425.
Cate et al., Isolation of the Bovine and Human Genes for Mullerian Inhibiting Substance and Expression of the Human Gene in Animal Cells, Cell, 1986, vol. 45, No. 4, p. 685–698.
Clackson et al., Making antibody fragments using phage display libraries, 1991, Nature 352:624–628.
Gubbary et al., A gene mapping to the sex–determining region of the mouse Y chromosome is a member of a novel family of embryonically expressed genes, Nature, Jul. 1990, Vol. 346, p. 245–250.
Jost A., Problems of Fetal Endocrinology: The Gonadal and hypophyseal Hormones, Academic Press, Inc., 1953, vol. III, p. 379–418.
Kintner C., Regulation of Embryonic Cell Adhesion by the Cadherin Cytoplasmic Domain, 1992, Cell., vol. 69, p. 225–236.
Koopman et al., Male development of chromosomally female mice transgenic for Sry, Nature, may 1991, vol. 351, p. 117–121.
Leyns et al., Frzb–1 Is a Secreted Antagonist of Wnt Signaling Expressed in the Spemann Organizer, 1997 Cell 88:747–756.
Griffiths et al., Human anti–self antibodies with high specificity from phage display libraries, 1993, EMBO J 12:725–734.
Goodfellow et al., Sry and Sex Determination in Mammals, Annu Rev. Genes, 1993, 27:71–92.
Hulsken et al., E–Cadherin and APC Compete for the Interaction with β–Catenin and the Cytoskeleton, The Journal of Cell Biology, 1994, vol. 127, No. 6, Part 2, p. 2061–2069.
Marks et al., Molecular Evolution of Proteins on Filamentous Phage, 1992, J. Biol. Chem. 267:16007–16010.
Lammers et al., Historical Development of Oral Contraceptives, Contraception 1998:57:1S–27S.
Lin et al., The Cysteine–rich frizzled domain of Frzb–1 is required and sufficient for modulation of Wnt signaling, 1997, Proc.Natl. Acad. Sci. vol. 94, pp. 11196–11200.
MacLean et al., Intersex disorders: shedding light on male sexual differentiation beyond SRY, Clinical Endocrinology, 1997, vol. 46, p. 101–108.
Masiakowski et al., The Wnk receptor CRD domain is also found in MuSK and related orphan receptor tyrosine kinases, Magazine R407.
Stark et al., Epithelial transformation of metanephric mesenchyme in the developing kidney regulated by Wnt–4, Nature, 1994, vol. 372, p. 679–683.

\* cited by examiner

*Primary Examiner*—Yvonne Eyler
*Assistant Examiner*—Michael Brannock
(74) *Attorney, Agent, or Firm*—Ingrid A. Beattie; Mintz Levin Cohn Ferris Glovsky & Popeo, P.C.

(57) ABSTRACT

A method of enhancing viability of an oocyte by contacting the oocyte with a Wnt-4 polypeptide.

3 Claims, No Drawings ing in the absence of the Wnt polypeptide. Preferably,

SEQUENCE LISTING

<160> NUMBER OF SEQ ID NOS: 11

<210> SEQ ID NO 1
<211> LENGTH: 133
<212> TYPE: PRT
<213> ORGANISM: Artificial Sequence
<220> FEATURE:
<223> OTHER INFORMATION: Synthetically generated
<220> FEATURE:
<221> NAME/KEY: VARIANT
<222> LOCATION: (1)...(133)
<223> OTHER INFORMATION: Xaa = Any Amino Acid
<220> FEATURE:
<221> NAME/KEY: VARIANT
<222> LOCATION: (2)...(10)
<223> OTHER INFORMATION: some amino acids may be absent
<220> FEATURE:
<221> NAME/KEY: VARIANT
<222> LOCATION: (12)...(53)
<223> OTHER INFORMATION: some amino acids may be absent
<220> FEATURE:
<221> NAME/KEY: VARIANT
<222> LOCATION: (70)...(79)
<223> OTHER INFORMATION: some amino acids may be absent
<220> FEATURE:
<221> NAME/KEY: VARIANT
<222> LOCATION: (85)...(91)
<223> OTHER INFORMATION: some amino acids may be absent
<220> FEATURE:
<221> NAME/KEY: VARIANT
<222> LOCATION: (93)...(119)
<223> OTHER INFORMATION: some amino acids may be absent
<220> FEATURE:
<221> NAME/KEY: VARIANT
<222> LOCATION: (121)...(133)
<223> OTHER INFORMATION: some amino acids may be absent

<400> SEQUENCE: 1

Cys Xaa Xaa Xaa Xaa Xaa Xaa Xaa Xaa Xaa Cys Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Cys Cys Cys Cys Cys Cys Cys Cys Cys Xaa Xaa
     50                  55                  60

Xaa Xaa Xaa Xaa Cys Xaa Xaa Xaa Xaa Xaa Xaa Xaa Xaa Xaa Xaa Cys
 65                  70                  75                  80

Xaa Xaa Xaa Cys Xaa Xaa Xaa Xaa Xaa Xaa Cys Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Cys Xaa Xaa Xaa Xaa Xaa Xaa Xaa Xaa
        115                 120                 125

Xaa Xaa Xaa Xaa Xaa
    130

<210> SEQ ID NO 2
<211> LENGTH: 136
<212> TYPE: PRT
<213> ORGANISM: Artificial Sequence
<220> FEATURE:
<223> OTHER INFORMATION: Synthetically generated
<220> FEATURE:
<221> NAME/KEY: VARIANT
<222> LOCATION: (1)...(136)

<223> OTHER INFORMATION: Xaa = Any Amino Acid

<400> SEQUENCE: 2

```
Cys Xaa Pro Xaa Xaa Xaa Xaa Xaa Cys Xaa Xaa Xaa Xaa Tyr
 1               5                  10                  15

Xaa Xaa Xaa Xaa Xaa Pro Asn Xaa Xaa His Xaa Xaa Xaa Xaa
            20              25                  30

Xaa Xaa Xaa Xaa Xaa Xaa Xaa Xaa Xaa Xaa Xaa Xaa Xaa Leu
        35                  40                  45

Xaa Xaa Xaa Xaa Cys Ser Xaa Xaa Xaa Xaa Phe Leu Cys Xaa Xaa
    50              55                  60

Xaa Xaa Pro Xaa Cys Xaa Xaa Xaa Xaa Xaa Xaa Xaa Xaa Xaa
65              70              75                  80

Pro Cys Arg Xaa Xaa Cys Glu Xaa Xaa Xaa Xaa Xaa Cys Xaa Xaa
            85                  90                  95

Xaa Xaa Xaa Xaa Xaa Xaa Xaa Xaa Xaa Xaa Xaa Xaa Xaa Xaa
            100                 105                 110

Xaa Xaa Xaa Trp Pro Xaa Xaa Xaa Xaa Cys Xaa Xaa Xaa Pro Xaa Xaa
        115                 120                 125

Xaa Xaa Xaa Xaa Xaa Xaa Xaa Cys
    130                 135
```

<210> SEQ ID NO 3
<211> LENGTH: 370
<212> TYPE: PRT
<213> ORGANISM: Homo sapiens

<400> SEQUENCE: 3

```
Met Gly Leu Trp Ala Leu Leu Pro Gly Trp Val Ser Ala Thr Leu Leu
 1               5                  10                  15

Leu Ala Leu Ala Ala Leu Pro Ala Ala Leu Ala Ala Asn Ser Ser Gly
            20                  25                  30

Arg Trp Trp Gly Ile Val Asn Val Ala Ser Ser Thr Asn Leu Leu Thr
        35                  40                  45

Asp Ser Lys Ser Leu Gln Leu Val Glu Pro Ser Leu Gln Leu Leu
    50                  55                  60

Ser Arg Lys Gln Arg Arg Leu Ile Arg Gln Asn Pro Gly Ile Leu His
65              70                  75                  80

Ser Val Ser Gly Gly Leu Gln Ser Ala Val Arg Glu Cys Lys Trp Gln
                85                  90                  95

Phe Arg Asn Arg Arg Trp Asn Cys Pro Thr Ala Pro Gly Pro His Leu
            100                 105                 110

Phe Gly Lys Ile Val Asn Arg Gly Cys Arg Glu Thr Ala Phe Ile Phe
        115                 120                 125

Ala Ile Thr Ser Ala Gly Val Thr His Ser Val Ala Arg Ser Cys Ser
    130                 135                 140

Glu Gly Ser Ile Glu Ser Cys Thr Cys Asp Tyr Arg Arg Arg Gly Pro
145                 150                 155                 160

Gly Gly Pro Asp Trp His Trp Gly Gly Cys Ser Asp Asn Ile Asp Phe
                165                 170                 175

Gly Arg Leu Phe Gly Arg Glu Phe Val Asp Ser Gly Glu Lys Gly Arg
            180                 185                 190

Asp Leu Arg Phe Leu Met Asn Leu His Asn Asn Glu Ala Gly Arg Thr
        195                 200                 205

Thr Val Phe Ser Glu Met Arg Gln Glu Cys Lys Cys His Gly Met Ser
```

```
          210                 215                 220
Gly Ser Cys Thr Val Arg Thr Cys Trp Met Arg Leu Pro Thr Leu Arg
225                 230                 235                 240

Ala Val Gly Asp Val Leu Arg Asp Arg Phe Asp Gly Ala Ser Arg Val
                245                 250                 255

Leu Tyr Gly Asn Arg Gly Ser Asn Arg Ala Ser Arg Ala Glu Leu Leu
                260                 265                 270

Arg Leu Glu Pro Glu Asp Pro Ala His Lys Pro Pro Ser Pro His Asp
            275                 280                 285

Leu Val Tyr Phe Glu Lys Ser Pro Asn Phe Cys Thr Tyr Ser Gly Arg
        290                 295                 300

Leu Gly Thr Ala Gly Thr Ala Gly Arg Ala Cys Asn Ser Ser Pro
305                 310                 315                 320

Ala Leu Asp Gly Cys Glu Leu Leu Cys Cys Gly Arg Gly His Arg Thr
                325                 330                 335

Arg Thr Gln Arg Val Thr Glu Arg Cys Asn Cys Thr Phe His Trp Cys
                340                 345                 350

Cys His Val Ser Cys Arg Asn Cys Thr His Thr Arg Val Leu His Glu
            355                 360                 365

Cys Leu
    370

<210> SEQ ID NO 4
<211> LENGTH: 360
<212> TYPE: PRT
<213> ORGANISM: Homo sapiens

<400> SEQUENCE: 4

Met Asn Ala Pro Leu Gly Gly Ile Trp Leu Trp Leu Pro Leu Leu Leu
  1               5                  10                  15

Thr Trp Leu Thr Pro Glu Val Asn Ser Ser Trp Trp Tyr Met Arg Ala
                20                  25                  30

Thr Gly Gly Ser Ser Arg Val Met Cys Asp Asn Val Pro Gly Leu Val
            35                  40                  45

Ser Ser Gln Arg Gln Leu Cys His Arg His Pro Asp Val Met Arg Ala
    50                  55                  60

Ile Ser Gln Gly Val Ala Glu Trp Thr Ala Glu Cys Gln His Gln Phe
65                  70                  75                  80

Arg Gln His Arg Trp Asn Cys Asn Thr Leu Asp Arg Asp His Ser Leu
                85                  90                  95

Phe Gly Arg Val Leu Leu Arg Ser Ser Arg Glu Ser Ala Phe Val Tyr
            100                 105                 110

Ala Ile Ser Ser Ala Gly Val Val Phe Ala Ile Thr Arg Ala Cys Ser
        115                 120                 125

Gln Gly Glu Val Lys Ser Cys Ser Cys Asp Pro Lys Lys Met Gly Ser
130                 135                 140

Ala Lys Asp Ser Lys Gly Ile Phe Asp Trp Gly Gly Cys Ser Asp Asn
145                 150                 155                 160

Ile Asp Tyr Gly Ile Lys Phe Ala Arg Ala Phe Val Asp Ala Lys Glu
                165                 170                 175

Arg Lys Gly Lys Asp Ala Arg Ala Leu Met Asn Leu His Asn Asn Arg
            180                 185                 190

Ala Gly Arg Lys Ala Val Lys Arg Phe Leu Lys Gln Glu Cys Lys Cys
        195                 200                 205
```

```
His Gly Val Ser Gly Ser Cys Thr Leu Arg Thr Cys Trp Leu Ala Met
        210                 215                 220

Ala Asp Phe Arg Lys Thr Gly Asp Tyr Leu Trp Arg Lys Tyr Asn Gly
225                 230                 235                 240

Ala Ile Gln Val Val Met Asn Gln Asp Gly Thr Gly Phe Thr Val Ala
                245                 250                 255

Asn Glu Arg Phe Lys Lys Pro Thr Lys Asn Asp Leu Val Tyr Phe Glu
            260                 265                 270

Asn Ser Pro Asp Tyr Cys Ile Arg Asp Arg Glu Ala Gly Ser Leu Gly
        275                 280                 285

Thr Ala Gly Arg Val Cys Asn Leu Thr Ser Arg Gly Met Asp Ser Cys
    290                 295                 300

Glu Val Met Cys Cys Gly Arg Gly Tyr Asp Thr Ser His Val Thr Arg
305                 310                 315                 320

Met Thr Lys Cys Gly Cys Lys Phe His Trp Cys Cys Ala Val Arg Cys
                325                 330                 335

Gln Asp Cys Leu Glu Ala Leu Asp Val His Thr Cys Lys Ala Pro Lys
            340                 345                 350

Asn Ala Asp Trp Thr Thr Ala Thr
        355                 360

<210> SEQ ID NO 5
<211> LENGTH: 133
<212> TYPE: PRT
<213> ORGANISM: Homo sapiens

<400> SEQUENCE: 5

Cys Lys Cys His Gly Leu Ser Gly Ser Cys Glu Val Lys Thr Cys Trp
1               5                   10                  15

Trp Ser Gln Pro Asp Phe Arg Ala Ile Gly Asp Phe Leu Lys Asp Lys
                20                  25                  30

Tyr Asp Ser Ala Ser Glu Met Val Val Glu Lys His Arg Glu Ser Arg
            35                  40                  45

Gly Trp Val Glu Thr Leu Arg Pro Arg Tyr Thr Tyr Phe Lys Val Pro
        50                  55                  60

Thr Glu Arg Asp Leu Val Tyr Tyr Glu Ala Ser Pro Asn Phe Cys Glu
65                  70                  75                  80

Pro Asn Pro Glu Thr Gly Ser Phe Gly Thr Arg Asp Arg Thr Cys Asn
                85                  90                  95

Val Ser Ser His Gly Ile Asp Gly Cys Asp Leu Leu Cys Cys Gly Arg
            100                 105                 110

Gly His Asn Ala Arg Ala Glu Arg Arg Arg Glu Lys Cys Arg Cys Val
        115                 120                 125

Phe His Trp Cys Cys
    130

<210> SEQ ID NO 6
<211> LENGTH: 120
<212> TYPE: PRT
<213> ORGANISM: Homo sapiens

<400> SEQUENCE: 6

Gly Val Ser Gly Ser Cys Glu Val Lys Thr Cys Trp Arg Ala Val Pro
1               5                   10                  15

Pro Phe Arg Gln Val Gly His Ala Leu Lys Glu Lys Phe Asp Gly Ala
                20                  25                  30
```

```
Thr Glu Val Glu Pro Arg Arg Val Gly Ser Ser Arg Ala Leu Val Pro
        35                  40                  45

Arg Asn Ala Gln Phe Lys Pro His Thr Asp Glu Asp Leu Val Tyr Leu
        50                  55                  60

Glu Pro Ser Pro Asp Phe Cys Glu Gln Asp Met Arg Ser Gly Val Leu
 65                  70                  75                  80

Gly Thr Arg Gly Arg Thr Cys Asn Lys Thr Ser Lys Ala Ile Asp Gly
                85                  90                  95

Cys Glu Leu Leu Cys Cys Gly Arg Gly Phe His Thr Ala Gln Val Glu
                100                 105                 110

Leu Ala Glu Arg Cys Ser Cys Lys
        115                 120

<210> SEQ ID NO 7
<211> LENGTH: 349
<212> TYPE: PRT
<213> ORGANISM: Homo sapiens

<400> SEQUENCE: 7

Met Asn Arg Lys Ala Leu Arg Cys Leu Gly His Leu Phe Leu Ser Leu
 1               5                  10                  15

Gly Met Val Cys Leu Arg Ile Gly Gly Phe Ser Ser Val Val Ala Leu
                20                  25                  30

Gly Ala Thr Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
        50                  55                  60

Gly Ser Gln Met Gly Leu Asp Glu Cys Gln Phe Gln Phe Arg Asn Gly
 65                  70                  75                  80

Arg Trp Asn Cys Ser Ala Leu Gly Glu Arg Thr Val Phe Gly Lys Glu
                85                  90                  95

Leu Lys Val Gly Ser Arg Asp Gly Ala Phe Thr Tyr Ala Ile Ile Ala
                100                 105                 110

Ala Gly Val Ala His Ala Ile Thr Ala Ala Cys Thr His Gly Asn Leu
            115                 120                 125

Ser Asp Cys Gly Cys Asp Lys Glu Lys Gln Gly Gln Tyr His Arg Asp
130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
                180                 185                 190

Glu Glu Asn Met Lys Leu Glu Cys Lys Cys His Gly Val Ser Gly Ser
            195                 200                 205

Cys Thr Thr Lys Thr Cys Trp Thr Thr Leu Pro Gln Phe Arg Glu Leu
        210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
                260                 265                 270

Lys Ser Pro Asn Tyr Cys Glu Glu Asp Pro Val Thr Gly Ser Val Gly
            275                 280                 285
```

```
Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
                340                 345

<210> SEQ ID NO 8
<211> LENGTH: 124
<212> TYPE: PRT
<213> ORGANISM: Homo sapiens

<400> SEQUENCE: 8

Gly Val Ser Gly Ser Cys Thr Thr Lys Thr Cys Trp Thr Thr Leu Pro
  1               5                  10                  15

Lys Phe Arg Glu Val Gly His Leu Leu Lys Glu Lys Tyr Asn Ala Ala
                 20                  25                  30

Val Gln Val Glu Val Val Arg Ala Ser Arg Leu Arg Gln Pro Thr Phe
             35                  40                  45

Leu Arg Ile Lys Gln Leu Arg Ser Tyr Gln Lys Pro Met Glu Thr Asp
         50                  55                  60

Leu Val Tyr Ile Glu Lys Ser Pro Asn Tyr Cys Glu Asp Ala Ala
 65                  70                  75                  80

Thr Gly Ser Val Gly Thr Gln Gly Arg Ile Cys Asn Arg Thr Ser Pro
                 85                  90                  95

Gly Ala Asp Gly Cys Asp Thr Met Cys Cys Gly Arg Gly Tyr Asn Thr
                100                 105                 110

His Gln Tyr Thr Lys Val Trp Gln Cys Asn Cys Lys
             115                 120

<210> SEQ ID NO 9
<211> LENGTH: 365
<212> TYPE: PRT
<213> ORGANISM: Homo sapiens

<400> SEQUENCE: 9

Met Ala Gly Ser Ala Met Ser Ser Lys Phe Phe Leu Val Ala Leu Ala
  1               5                  10                  15

Ile Phe Phe Ser Phe Ala Gln Val Val Ile Glu Ala Asn Ser Trp Trp
                 20                  25                  30

Ser Leu Gly Met Asn Asn Pro Val Gln Met Ser Glu Val Tyr Ile Ile
             35                  40                  45

Gly Ala Gln Pro Leu Cys Ser Gln Leu Ala Gly Leu Ser Gln Gly Gln
         50                  55                  60

Lys Lys Leu Cys His Leu Tyr Gln Asp His Met Gln Tyr Ile Gly Glu
 65                  70                  75                  80

Gly Ala Lys Thr Gly Ile Lys Glu Cys Gln Tyr Gln Phe Arg His Arg
                 85                  90                  95

Arg Trp Asn Cys Ser Thr Val Asp Asn Thr Ser Val Phe Gly Arg Val
                100                 105                 110

Met Gln Ile Gly Ser Arg Glu Thr Ala Phe Thr Tyr Ala Val Ser Ala
             115                 120                 125

Ala Gly Val Val Asn Ala Met Ser Arg Ala Cys Arg Glu Gly Glu Leu
         130                 135                 140
```

-continued

```
Ser Thr Cys Gly Cys Ser Arg Ala Ala Arg Pro Lys Asp Leu Pro Arg
145                 150                 155                 160

Asp Trp Leu Trp Gly Gly Cys Gly Asp Asn Ile Asp Tyr Gly Tyr Arg
                165                 170                 175

Phe Ala Lys Glu Phe Val Asp Ala Arg Glu Arg Glu Arg Ile His Ala
            180                 185                 190

Lys Gly Ser Tyr Glu Ser Ala Arg Ile Leu Met Asn Leu His Asn Asn
        195                 200                 205

Glu Ala Gly Arg Arg Thr Val Tyr Asn Leu Ala Asp Val Ala Cys Lys
    210                 215                 220

Cys His Gly Val Ser Gly Ser Cys Ser Leu Lys Thr Cys Trp Leu Gln
225                 230                 235                 240

Leu Ala Asp Phe Arg Lys Val Gly Asp Ala Leu Lys Glu Lys Tyr Asp
                245                 250                 255

Ser Ala Ala Met Arg Leu Asn Ser Arg Gly Lys Leu Val Gln Val
                260                 265                 270

Asn Ser Arg Phe Asn Ser Pro Thr Thr Gln Asp Leu Val Tyr Ile Asp
            275                 280                 285

Pro Ser Pro Asp Tyr Cys Val Arg Asn Glu Ser Thr Gly Ser Leu Gly
        290                 295                 300

Thr Gln Gly Arg Leu Cys Asn Lys Thr Ser Glu Gly Met Asp Gly Cys
305                 310                 315                 320

Glu Leu Met Cys Cys Gly Arg Gly Tyr Asp Gln Phe Lys Thr Val Gln
                325                 330                 335

Thr Glu Arg Cys His Cys Lys Phe His Trp Cys Cys Tyr Val Lys Cys
            340                 345                 350

Lys Lys Cys Thr Glu Ile Val Asp Gln Phe Val Cys Lys
        355                 360                 365

<210> SEQ ID NO 10
<211> LENGTH: 781
<212> TYPE: PRT
<213> ORGANISM: Homo sapiens

<400> SEQUENCE: 10

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
```

-continued

```
           145                 150                 155                 160

Asn Asp Glu Asp Gln Val Val Asn Lys Ala Ala Val Met Val His
                    165                 170                 175

Gln Leu Ser Lys Lys Glu Ala Ser Arg His Ala Ile Met Arg Ser Pro
                180                 185                 190

Gln Met Val Ser Ala Ile Val Arg Thr Met Gln Asn Thr Asn Asp Val
                195                 200                 205

Glu Thr Ala Arg Cys Thr Ala Gly Thr Leu His Asn Leu Ser His His
            210                 215                 220

Arg Glu Gly Leu Leu Ala Ile Phe Lys Ser Gly Ile Pro Ala Leu
    225                 230                 235                 240

Val Lys Met Leu Gly Ser Pro Val Asp Ser Val Leu Phe Tyr Ala Ile
                    245                 250                 255

Thr Thr Leu His Asn Leu Leu His Gln Glu Gly Ala Lys Met Ala
                260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
        290                 295                 300

Ala Tyr Gly Asn Gln Glu Ser Lys Leu Ile Ile Leu Ala Ser Gly Gly
    305                 310                 315                 320

Pro Gln Ala Leu Val Asn Ile Met Arg Thr Tyr Thr Tyr Glu Lys Leu
                    325                 330                 335

Leu Trp Thr Thr Ser Arg Val Leu Lys Val Leu Ser Val Cys Ser Ser
                340                 345                 350

Asn Lys Pro Ala Ile Val Glu Ala Gly Gly Met Gln Ala Leu Gly Leu
                355                 360                 365

His Leu Thr Asp Pro Ser Gln Arg Leu Val Gln Asn Cys Leu Trp Thr
        370                 375                 380

Leu Arg Asn Leu Ser Asp Ala Ala Thr Lys Gln Glu Gly Met Glu Gly
    385                 390                 395                 400

Leu Leu Gly Thr Leu Val Gln Leu Leu Gly Ser Asp Asp Ile Asn Val
                    405                 410                 415

Val Thr Cys Ala Ala Gly Ile Leu Ser Asn Leu Thr Cys Asn Asn Tyr
                420                 425                 430

Lys Asn Lys Met Met Val Cys Gln Val Gly Gly Ile Glu Ala Leu Val
                435                 440                 445

Arg Thr Val Leu Arg Ala Gly Asp Arg Glu Asp Ile Thr Glu Pro Ala
        450                 455                 460

Ile Cys Ala Leu Arg His Leu Thr Ser Arg His Gln Glu Ala Glu Met
    465                 470                 475                 480

Ala Gln Asn Ala Val Arg Leu His Tyr Gly Leu Pro Val Val Lys
                    485                 490                 495

Leu Leu His Pro Pro Ser His Trp Pro Leu Ile Lys Ala Thr Val Gly
                500                 505                 510

Leu Ile Arg Asn Leu Ala Leu Cys Pro Ala Asn His Ala Pro Leu Arg
                515                 520                 525

Glu Gln Gly Ala Ile Pro Arg Leu Val Gln Leu Leu Val Arg Ala His
        530                 535                 540

Gln Asp Thr Gln Arg Arg Thr Ser Met Gly Gly Thr Gln Gln Gln Phe
    545                 550                 555                 560

Val Glu Gly Val Arg Met Glu Glu Ile Val Glu Gly Cys Thr Gly Ala
                    565                 570                 575
```

```
Leu His Ile Leu Ala Arg Asp Val His Asn Arg Ile Val Ile Arg Gly
            580                 585                 590
Leu Asn Thr Ile Pro Leu Phe Val Gln Leu Leu Tyr Ser Pro Ile Glu
            595                 600                 605
Asn Ile Gln Arg Val Ala Ala Gly Val Leu Cys Glu Leu Ala Gln Asp
            610                 615                 620
Lys Glu Ala Ala Glu Ala Ile Glu Ala Glu Gly Ala Thr Ala Pro Leu
625                 630                 635                 640
Thr Glu Leu Leu His Ser Arg Asn Glu Gly Val Ala Thr Tyr Ala Ala
                645                 650                 655
Ala Val Leu Phe Arg Met Ser Glu Asp Lys Pro Gln Asp Tyr Lys Lys
            660                 665                 670
Arg Leu Ser Val Glu Leu Thr Ser Ser Leu Phe Arg Thr Glu Pro Met
            675                 680                 685
Ala Trp Asn Glu Thr Ala Asp Leu Gly Leu Asp Ile Gly Ala Gln Gly
            690                 695                 700
Glu Pro Leu Gly Tyr Arg Gln Asp Asp Pro Ser Tyr Arg Ser Phe His
705                 710                 715                 720
Ser Gly Gly Tyr Gly Gln Asp Ala Leu Gly Met Asp Pro Met Met Glu
                725                 730                 735
His Glu Met Gly Gly His His Pro Gly Ala Asp Tyr Pro Val Asp Gly
            740                 745                 750
Leu Pro Asp Leu Gly His Ala Gln Asp Leu Met Asp Gly Leu Pro Pro
            755                 760                 765
Gly Asp Ser Asn Gln Leu Ala Trp Phe Asp Thr Asp Leu
770                 775                 780
```

<210> SEQ ID NO 11
<211> LENGTH: 906
<212> TYPE: PRT
<213> ORGANISM: Homo sapiens

<400> SEQUENCE: 11

```
Met Cys Arg Ile Ala Gly Ala Leu Arg Thr Leu Leu Pro Leu Leu Leu
 1               5                  10                  15
Ala Leu Leu Gln Ala Ser Val Glu Ala Ser Gly Glu Ile Ala Leu Cys
            20                  25                  30
Lys Thr Gly Phe Pro Glu Asp Val Tyr Ser Ala Val Leu Ser Lys Asp
            35                  40                  45
Val His Glu Gly Gln Pro Leu Leu Asn Val Lys Phe Ser Asn Cys Asn
         50                  55                  60
Gly Lys Arg Lys Val Gln Tyr Glu Ser Ser Glu Pro Ala Asp Phe Lys
 65                  70                  75                  80
Val Asp Glu Asp Gly Met Val Tyr Ala Val Arg Ser Phe Pro Leu Ser
                 85                  90                  95
Ser Glu His Ala Lys Phe Leu Ile Tyr Ala Gln Asp Lys Glu Thr Gln
            100                 105                 110
Glu Lys Trp Gln Val Ala Val Lys Leu Ser Leu Lys Pro Thr Leu Thr
            115                 120                 125
Glu Glu Ser Val Lys Glu Ser Ala Glu Val Glu Glu Ile Val Phe Pro
            130                 135                 140
Arg Gln Phe Ser Lys His Ser Gly His Leu Gln Arg Gln Lys Arg Asp
145                 150                 155                 160
Trp Val Ile Pro Pro Ile Asn Leu Pro Glu Asn Ser Arg Gly Pro Phe
```

-continued

```
                165                 170                 175
Pro Gln Glu Leu Val Arg Ile Arg Ser Asp Arg Asp Lys Asn Leu Ser
                    180                 185                 190

Leu Arg Tyr Ser Val Thr Gly Pro Gly Ala Asp Gln Pro Pro Thr Gly
            195                 200                 205

Ile Phe Ile Ile Asn Pro Ile Ser Gly Gln Leu Ser Val Thr Lys Pro
        210                 215                 220

Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
            260                 265                 270

Asn Gly Thr Val Pro Glu Gly Ser Lys Pro Gly Thr Tyr Val Met Thr
        275                 280                 285

Val Thr Ala Ile Asp Ala Asp Asp Pro Asn Ala Leu Asn Gly Met Leu
    290                 295                 300

Arg Tyr Arg Ile Val Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                325                 330                 335

Leu Asp Arg Glu Lys Val Gln Gln Tyr Thr Leu Ile Ile Gln Ala Thr
            340                 345                 350

Asp Met Glu Gly Asn Pro Thr Tyr Gly Leu Ser Asn Thr Ala Thr Ala
        355                 360                 365

Val Ile Thr Val Thr Asp Val Asn Asp Asn Pro Pro Glu Phe Thr Ala
    370                 375                 380

Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
                405                 410                 415

Asn Ala Val Tyr Arg Ile Ser Gly Gly Asp Pro Thr Gly Arg Phe Ala
            420                 425                 430

Ile Gln Thr Asp Pro Asn Ser Asn Asp Gly Leu Val Thr Val Val Lys
        435                 440                 445

Pro Ile Asp Phe Glu Thr Asn Arg Met Phe Val Leu Thr Val Ala Ala
    450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                485                 490                 495

Phe Ala Pro Asn Pro Lys Ile Ile Arg Gln Glu Glu Gly Leu His Ala
            500                 505                 510

Gly Thr Met Leu Thr Thr Phe Thr Ala Gln Asp Pro Asp Arg Tyr Met
        515                 520                 525

Gln Gln Asn Ile Arg Tyr Thr Lys Leu Ser Asp Pro Ala Asn Trp Leu
    530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
                565                 570                 575

Ala Ser Asp Asn Gly Ile Pro Pro Met Ser Gly Thr Gly Thr Leu Gln
            580                 585                 590
```

-continued

```
Ile Tyr Leu Leu Asp Ile Asn Asp Asn Ala Pro Gln Val Leu Pro Gln
        595                 600                 605

Glu Ala Glu Thr Cys Glu Thr Pro Asp Pro Asn Ser Ile Asn Ile Thr
        610                 615                 620

Ala Leu Asp Tyr Asp Ile Asp Pro Asn Ala Gly Pro Phe Ala Phe Asp
625                 630                 635                 640

Leu Pro Leu Ser Pro Val Thr Ile Lys Arg Asn Trp Thr Ile Thr Arg
                645                 650                 655

Leu Asn Gly Asp Phe Ala Gln Leu Asn Leu Lys Ile Lys Phe Leu Glu
                660                 665                 670

Ala Gly Ile Tyr Glu Val Pro Ile Ile Ile Thr Asp Ser Gly Asn Pro
            675                 680                 685

Pro Lys Ser Asn Ile Ser Ile Leu Arg Val Lys Val Cys Gln Cys Asp
        690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Leu Cys Ile Ile Ile Leu Leu
                725                 730                 735

Ile Leu Val Leu Met Phe Val Val Trp Met Lys Arg Arg Asp Lys Glu
                740                 745                 750

Arg Gln Ala Lys Gln Leu Leu Ile Asp Pro Glu Asp Asp Val Arg Asp
            755                 760                 765

Asn Ile Leu Lys Tyr Asp Glu Glu Gly Gly Glu Glu Asp Gln Asp
        770                 775                 780

Tyr Asp Leu Ser Gln Leu Gln Gln Pro Asp Thr Val Glu Pro Asp Ala
785                 790                 795                 800

Ile Lys Pro Val Gly Ile Arg Arg Met Asp Glu Arg Pro Ile His Ala
                805                 810                 815

Glu Pro Gln Tyr Pro Val Arg Ser Ala Ala Pro His Pro Gly Asp Ile
            820                 825                 830

Gly Asp Phe Ile Asn Glu Gly Leu Lys Ala Ala Asp Asn Asp Pro Thr
        835                 840                 845

Ala Pro Pro Tyr Asp Ser Leu Leu Val Phe Asp Tyr Glu Gly Ser Gly
    850                 855                 860

Ser Thr Ala Gly Ser Leu Ser Ser Leu Asn Ser Ser Ser Ser Gly Gly
865                 870                 875                 880

Glu Gln Asp Tyr Asp Tyr Leu Asn Asp Trp Gly Pro Arg Phe Lys Lys
                885                 890                 895

Leu Ala Asp Met Tyr Gly Gly Gly Asp Asp
            900                 905
```

WNT SIGNALLING IN REPRODUCTIVE ORGANS This application claims priority from provisional application Ser. No. 60/104,355, filed on Oct. 15, 1998.

STATEMENT AS TO FEDERALLY SPONSORED RESEARCH

This invention was made at least in part with funds from the Federal Government under grant number HD30249 from the National Institutes of Health. The Government therefore has certain rights in the invention.

BACKGROUND OF THE INVENTION

The invention relates to reproductive biology.

Wnt polypeptides are secreted cysteine-rich glycosylated polypeptides that play a role in the development of a wide range of organisms. The Wnt family of polypeptides contains at least 16 mammalian members which bind to an extracellular domain of a family of cell surface proteins called Frizzled receptors. Wnt polypeptides may play a role in embryonic induction, generation of cell polarity, and specification of cell fate.

SUMMARY OF THE INVENTION

The invention is based on the discovery that Wnt signalling is involved in the development of female reproductive organs in the embryo and in oocyte development in adult animals. Accordingly, the invention features a method of contraception which is carried out by administering to a female primate an antagonist of a Wnt polypeptide. The antagonist inhibits Wnt-signalling which plays a role in oocyte development and, in turn, inhibits oocyte development. Preferably, the Wnt polypeptide is Wnt-1 class polypeptide such as Wnt-1, Wnt-2, Wnt-3a, Wnt-4, Wnt-7a, or Wnt-7b polypeptide.

A Wnt antagonist is a composition which inhibits the physiological activity of a Wnt polypeptide. For example, the activity is preferably Wnt signalling by a Wnt-1 class polypeptide. A Wnt antagonist inhibits oocyte development in an adult female animal and is therefore useful as a contraceptive. A Wnt antagonist binds to a Wnt polypeptide or to its receptor or to another component of the Wnt-1 class signal transduction pathway but fails to potentiate Wnt-signalling. For example, the Wnt antagonist is a dominant negative N-cadherin mutant, a dominant negative β-catenin mutant, or a Frizzled polypeptide. Antagonistic polypeptides may contain a cysteine-rich domain, e.g., a peptide having an amino acid sequence with at least 5%, preferably at least 7%, and most preferably at least 8%, cysteines. The polypeptide preferably contains at least 5 cysteines, more preferably at least 8 cysteines, and most preferably at least 10 cysteines. For example, the polypeptide is about 120 amino acids in length and contains 10 cysteines. Preferably, the polypeptide contains the amino acid consensus sequence of $CX_{7-9}CX_{36-42}C_8CX_6CX_{6-10}CX_3CX_{6-7}CX_{12-27}CX_{8-13}$ (SEQ ID NO: 1) or CXPXXXXXXX CXXXXYXXXX XPNXXXHXXX XXXXXXXXXX XXXXXXXLXX XXCSXXXXXF LCXXXXPXCX XXXXXXXXXX PCRXXCEXXX XXXCXXXXXX XXXXXXXXXX XXXXXWPXXX XCXXXPXXXX XXXXXC (SEQ ID NO:2). Preferably, the polypeptide has at least 30%, more preferably at least 40%, more preferably at least 50%, more preferably at least 75% identity to the cysteine-rich domain of a Frizzled receptor. Sequence identity is determined using the Sequence Analysis Software Package of the Genetics Computer Group, University of Wisconsin Biotechnology Center, 1710 University Avenue, Madison, Wis. 53705), with the default parameters as specified therein. Other Wnt antagonists include Wnt-specific antibodies, e.g., an antibody which binds to a Wnt polypeptide and inhibits oocyte development, and Wnt-5a class polypeptides.

The invention also includes a contraceptive vaccine. The vaccine contains a Wnt polypeptide, e.g., Wnt-1, Wnt-2, Wnt-3a, Wnt-4, Wnt-7a, or Wnt-7b. The Wnt polypeptide is characterized as binding to an antibody that inhibits Wnt-signalling, and thereby, oocyte development.

Wnt polypeptides, e.g., Wnt-4 and Wnt-7a, promote oocyte development. Thus, a method of promoting maturation of an immature oocyte by contacting the oocyte with a substantially pure preparation of a Wnt polypeptide, e.g., Wnt-1, Wnt-2, Wnt-3a, Wnt-4, Wnt-7a, or Wnt-7b polypeptide, is also within the invention. Polypeptides or other compounds are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity is measured by any appropriate standard method, e.g., by column chromatography, polyacrylamide gel electrophoresis, or HPLC analysis.

Wnt polypeptides are also used to enhance viability of an oocyte, e.g., an oocyte to be used in an in vitro fertilization (IVF) procedure. The oocyte is contacted with w Wnt polypeptide either in vivo prior to retrieval or in vitro prior to the IVF procedure. For example, the viability of a cryopreserved oocyte is enhanced by contacting the oocyte with a Wnt polypeptide during and/or subsequent to thawing. Wnt polypeptides are also used to increase the number of mature oocytes by culturing a sample containing immature oocytes in a culture medium which includes a Wnt polypeptide. The oocytes are cultured in the presence of a Wnt polypeptide for at least one hour and up to several days. Following culture, the number of mature oocytes in the sample cultured in the presence of said Wnt polypeptide is at least 50% greater than the number of mature oocytes cultured in the absence of the Wnt polypeptide. Preferably, the increase in the number of mature oocytes in the sample is at least 75%, more preferably 100%, and most preferably 200% greater than the number of mature oocytes cultured in the absence of the Wnt polypeptide.

Other features and advantages of the invention will be apparent from the following description of the preferred embodiments thereof, and from the claims.

DETAILED DESCRIPTION

The data described herein indicate that Wnt-signaling by Wnt-1 class polypeptides, e.g., Wnt-4 and Wnt-7a, is involved in the development of female reproductive organs in the embryo and in oocyte development in adult animals.

EXAMPLE 1

Female Development in Mammals Regulated by Wnt-4 Signaling

In the mammalian embryo, both sexes are initially morphologically indistinguishable, and specific hormones are required for sex specific development. MIS and testosterone secreted by the differentiating embryonic testes results in the loss of female (Müllerian) and promotion of male (Wolffian) reproductive duct development, respectively.

The data described herein demonstrate that Wnt-4 signaling also plays a pivotal role in female sexual development. At birth, Wnt-4 mutant males appear normal, whereas Wnt-4 mutant females are masculinized; the Müllerian duct is absent, while the Wolffian duct continues to develop. Initially, Wnt-4 is required in both sexes for formation of the Müllerian duct. Next, Wnt-4 activity in the developing ovary appears to suppress Leydig cell development. Consequently, Wnt-4 mutant females ectopically activate the testosterone biosynthetic pathway. Finally, the data indicate that Wnt-4 is required for maintenance of the female germ line. These studies indicate that establishment of sexual dimorphism is under the control of both local and systemic signals.

Early in fetal life, the reproductive system of male and female mammalian embryos consists of an indifferent gonad, indistinguishable by morphological criteria between the sexes. Adjacent to the gonads are two simple ducts, the Müllerian and Wolffian ducts, the anlagen of female (ovary, uterus, and upper part of the vagina) and male (epididymis, vas deferens and seminal vesicles) reproductive tract, respectively. Thus, the embryo is initially sexually indifferent. Correct sexual development is dependent on differentiation of somatic cell lineage in the gonad and the appropriate production, reception and response to gonadal hormones.

Male gonadal differentiation is triggered by the action of the Y chromosome encoded testis determining factor (SRY) in the supporting cell lineage of the testis. This results in the differentiation of Sertoli cell precursors, and the secretion of a hormone, Müllerian inhibiting substance (MIS), which induces regression of the Müllerian duct. The interstitial cell lineage gives rise to steroid cell precursors. In the testis, their differentiation into Leydig cell precursors leads to production of testosterone which promotes the development of Wolffian duct derivatives. In the female, absence of MIS permits continued development of the Müllerian duct, while absence of testosterone leads to degeneration of the Wolffian duct. Thus, the female pathway of development has traditionally been considered a default state resulting primarily from the absence of the testis determining factor, and as a consequence, the failure of MIS and testosterone synthesis. However, the data described below indicate that other factors are involved in the pathway. For example, Wnt-4 and Wnt-7a, play an important role in the development of female reproductive organs in the embryo and in oocyte development in adult animals.

Wnt-4, a member of the Wnt-family of locally acting cell signals, is essential for development of the female and suppression of the male reproductive system. Wnt-4 has now been found to play a key role in the female pathway of sexual development by regulating Müllerian duct formation, controlling steroidogenesis in the gonad and supporting oocyte development.

The role of Wnt-4 in development of female reproductive organs, steriodogenesis, and oocyte development was determined as follows.

Genotyping and Sex Typing of Embryos

A Wnt-4 mutant mouse line and Wnt-4 mutant embryos were made and genotyped using methods known in the art, e.g., Stark et al., 1994, Nature 372:679–683. For sex typing, embryos were collected separately, DNA was isolated by routine methods from either the yolk sac, or remainder of the embryo after removal of the urogenital system and digested with EcoRI. Y-chromosome specific sequences were detected by Southern blot hybridization with the Y-chromosome repetitive probe, pY353/B41. After genotyping and sex typing, samples were pooled accordingly. The Pax-2 transgenic mouse line (Kispert et al., 1996, Development 122:3627–2627) was typed using a Lac Z cDNA probe.

Histology in situ Hybridization, β-galactosidase and Antibody Staining:

Histological procedures, whole mount and section in situ hybridization and β-galactosidase staining were performed according to routine procedures. An antibody which binds to germ cell nuclear antigen (GCNA)-1 was used at a concentration of 1 in 1,000, and antibody binding visualized using a Vectastain ABC kit according to the manufacturer's recommendations.

Characterization of Sex Specific and Sex Independent Expression of Wnt-4

Wnt-4 expression was detected in the kidney as well as in the mesonephros, which participates in gonad formation, in the gonad itself, and in association with the Müllerian duct.

Prior to gonad formation at 9.5 and 10.5 days post coitum (dpc) in the mouse, Wnt-4 was found to be expressed along the length of the mesonephros in the mesenchyme but not in mesonephric tubules. In the region of the presumptive gonad, expression was also observed in the coelomic epithelium. As the gonads emerged at 11.0 dpc, Wnt-4 was expressed in the mesenchyme of the indifferent gonad in both sexes and in the mesonephros, but was absent from the mesonephric tubules and Wolffian duct. A second Wnt family member, Wnt-6 was also expressed in the genital ridge. At this stage of development, the Müllerian duct was not visible; the duct formed over the next 24 hours by an in-folding of Wnt-4 expressing coelomic epithelium. When sex specific differentiation of the gonads commenced around 11.5 dpc, Wnt-4 expression was down-regulated in the male, and maintained in the female gonad. Sexually dimorphic expression continued over the period in which the sexes become morphologically distinct. Examination of Wnt-4 expression in the ovaries of Steele (S1) mutant embryos, which are germ cell deficient, indicated that Wnt-4 expression is either partly or completely within somatic cell lineages. In contrast to the gonads, Wnt-4 expression was maintained in the mesonephric mesenchyme of both sexes from where some of the gonadal somatic lineages are thought to emerge. In the region of the developing sex ducts, Wnt-4 was absent from the Wolffian duct epithelium and mesenchyme, but was strongly expressed in mesenchyme cells underlying the newly formed Müllerian duct which itself expressed high levels of a second Wnt family member, Wnt-7a, and the transcriptional regulator, Pax 8. Expression in the duct and in the ovary was maintained throughout fetal life.

Masculinization of Wnt-4 Mutant Females

The sex specific regulation of Wnt-4 in the gonad and sex independent expression of Wnt-4 in the mesenchyme of the mesonephros and Müllerian duct suggested that Wnt-4 plays a role in development of the reproductive system. To address this issue, the urogenital systems from progeny of heterozygous intercrosses between mice carrying a likely null allele of Wnt-4 were collected. As mice which are homozygous for this mutation die of kidney failure shortly after birth, pups were examined at 18.5 dpc and at birth. Genotype and sex were initially scored by phenotypic inspection of internal reproductive organs and subsequently determined unambiguously by Southern blot analysis with Wnt-4 and Y-chromosome specific probes.

At birth the reproductive organs of male and female pups are distinct. The testis were round in appearance with prominent Sertoli cell generated sex cords ensheathing the germ cells. The proximal Wolffian duct which corresponds to the developing epididymis was highly coiled. Testis and ductal development in Wnt-4 mutant males were morphologically indistinguishable from wild-type and heterozygous male siblings. Further, expression of the Sertoli cell markers MIS21 and Desert hedgehog (Dhh), Leydig cell marker, 3β-hydroxysteroid dehydrogenase (3b-HSD), and Wolffian duct specific expression of Sonic hedgehog, (Shh) 24 were found to be unaltered. Thus, male development was unaffected by the loss of Wnt-4.

Normal females were observed to have an elongated ovary which lies closer to the kidney than does the testis. The ovary was covered by an outer coelomic epithelial capsule. In contrast to the Wolffian duct of the male, the proximal region of the Müllerian duct had only two or three large coils where oviduct formation has commenced. Whereas females heterozygous for the Wnt-4 mutant allele were similar to their wild-type siblings, the gonad and proximal sex ducts of homozygotes appeared masculinized. In most cases, the gonad of mutant females was in its correct position but developed closely associated with a fat body typical of the male. Further, the gonad was round and unencapsulated like that of the male, and the single gonadal associated duct had a highly convoluted proximal region resembling the developing epididymal region of the male Wolffian duct. In contrast to the internal organs, no masculinization of the external genitalia of Wnt-4 mutant females was evident at birth.

To determine the identity of the gonad associated duct in Wnt-4 mutant females, expression of a Pax2lacZ transgene, which is expressed in the Wolffian duct and its derivatives, as well as in the collecting duct system and ureter of the kidney was evaluated. As expected, the transgene was expressed in the Wolffian duct of wild type and Wnt-4 mutant males and was absent from wild-type females after Wolffian duct regression. In contrast, the transgene was expressed in the single duct of Wnt-4 mutant females, indicating that this duct was indeed the Wolffian duct, a conclusion further supported by expression of Shh, a second Wolffian duct marker. Thus, the external appearance of the gonad with associated fat pad, the absence of a Müllerian duct and the development of a Wolffian duct was indicative of a reversal of sexual development in Wnt-4 mutant females.

Wnt-4 is Required for Müllerian Duct Formation

Development of the sex ducts in mammals dependent on a poorly understood sex independent morphogenesis of the ductal systems, and a subsequent hormone-dependent modification which relies on correct differentiation of somatic cell lineages in the gonad. To investigate the fate of the Müllerian duct in Wnt-4 mutants, Wnt-4 mutants of both sexes at 14.5 dpc, one day prior to the MIS-induced apoptosis of the Müllerian duct in males, were examined. Müllerian duct development was identified by the expression of Wnt-7a, which is essential for sexually dimorphic development of this duct and Pax-8. The Müllerian duct was present in wild-type and heterozygous mice of both sexes as expected, but was absent from both mutant females and males. The absence of Wnt-7a and Pax-8 expression in identifiable Müllerian ducts at 12.5 dpc, or at 11.5 dpc (when the rostral region of the duct first forms) indicated that Wnt-4 signaling was required for the initial stages of ductal morphogenesis. These data indicate that Wnt-4 is essential in both sexes for Müllerian duct formation, although it is only in females that this deficiency has a significant consequence.

Steroidogenesis in Wnt-4 Mutant Females

Wolffian duct development depends upon steroid biosynthesis although it is not clear whether testosterone itself or an intermediate such as androstenedione represents the early bioactive male steroid. As Wnt-4 was not expressed in the Wolffian duct, continued development of this duct in mutant females indicated that Wnt-4 expression in the ovary plays a role in the control of steroidogenesis.

Testosterone biosynthesis in Leydig cells of the testes is dependent upon the expression of the several enzymes. For example, 3β-HSD converts pregnenolone to progesterone, an intermediate in testosterone biosynthesis. A deficiency in 3β-HSD consequently leads to male pseudohermaphrodism. 3β-HSD was found to be strongly expressed in Leydig cell precursors in the testes from 12.5 dpc. In the wild-type female, expression was absent from the ovary, but present in the adrenal gland where 3β-HSD is associated with the synthesis of mineralocorticoids and glucocorticoids. In contrast, 3β-HSD was expressed in the ovary of Wnt-4 mutant females from 12.5 dpc until birth. Ectopic activation of two other genes (17a-hydroxylase and the type III isoform of 17b-hydroxysteroid dehydrogenase (17b-HSD) which encodes the enzyme responsible for the conversion of androstenedione to testosterone was also observed. Thus, in the absence of Wnt-4 signaling, steroidogenesis was initiated in the ovary. These data indicate that biosynthesis and secretion of testosterone by the ovary promotes Wolffian duct development in Wnt-4 mutant females, although levels may be insufficient to masculinize external genitalia. The ectopic activation of steroidogenesis reflects either premature differentiation of thecal and/or granulosa cells (which require the same steroid intermediates for estradiol synthesis later in the mature ovary) or the inappropriate differentiation of Leydig cell precursors in the ovary. As the type III isoform of 17b-HSD is exclusively expressed in Leydig cells during normal mouse development, it appears that, in the absence of Wnt-4, interstitial cells in the ovary adopt a male Leydig cell fate.

To address whether the supporting cell lineage in the ovary of Wnt-4 mutants has undergone a primary sex-reversal which may subsequently lead to a secondary change in interstitial cell fates, expression of Dhh, MIS and Sox-9 (all of which are pre-Sertoli cell markers specifically expressed in the supporting cell lineage of the testes) was measured. None of these genes were ectopically activated in the ovaries of Wnt-4 mutants prior to normal loss of the Wolffian duct. This result, together with the absence of morphologically identifiable sex cords (at the time ectopic steroidogenic gene expression was first observed at 12.5 dpc) indicates that the ovaries of Wnt-4 mutants have not undergone a primary sex reversal leading to Sertoli cell development. Expression of Dax-1, which is implicated in the female pathway of sex determination, was still detected. However, several female characteristics were altered. For example, ovary specific expression of Msx-1 was detected at 14.5 dpc, but expression was lost from the ovary of Wnt-4 mutants. Thus, Wnt-4 signaling not only suppresses Leydig cell development in the developing ovary but also supports female-specific characteristics of gonadal gene expression.

Wnt-4 Supports Oocyte Development

In addition to alterations in steroidogenesis, a marked reduction in oocyte development was observed in mutant females. Germ cells enter the gonads between 10.5 and 12.5 dpc. In the female, germ cells enter meiotic prophase progressing to the diplotene stage by birth. In the male, after an initial proliferative phase they enter mitotic arrest. In situ hybridization at 14.5 dpc with Oct4, a germ cell marker, indicated normal numbers of germ cells in both the ovary and testes of Wnt-4 mutants. Consequently, the early phases of germ cell migration and proliferation were unaltered. In contrast, at birth, wild type or heterozygous females had a large number of readily detectable meiotic stage cortical oocytes, whereas the ovaries of Wnt-4 mutant females had only a few and those few were degenerating. The specific loss of oocytes was confirmed by staining testes and ovaries with an antibody which binds to the anti-GCNA-1. Whereas no differences were observed in the testes, Wnt-4 mutant ovaries had less than 10% of the oocytes scored in wild-type or heterozygous siblings. As chronic administration of testosterone does not impair oocyte development, the data indicated that the loss of oocytes was not a secondary consequence of altered interstitial cell fates, but reflected a direct role for Wnt-4 in promoting and maintaining development of the female germ line.

The loss of oocytes leads to a secondary sex-reversal of supporting cell lineages, and continued interactions between the oocyte and supporting cells are necessary for maintaining follicle cell and suppressing Sertoli cell fates. Consistent with this observation, few sex cord-like structures were found to emerge in oocyte depleted ovaries of Wnt-4 mutants at birth. Moreover, in contrast to the wild-type ovary, expression of the Sertoli cell markers, MIS and Dhh were detected in Wnt-4 mutants. Thus, although no apparent sex reversal was observed in the supporting cell lineage of the Wnt-4 mutant ovary earlier in development, some supporting cells adopted Sertoli cell characteristics after the loss of oocytes.

The data described herein indicate that Wnt-signaling plays a role in female development. Wnt-4 is required for three distinct aspects of the female pathway: (1) formation of the Müllerian duct, (2) differentiation of the interstitial cell lineage, and (3) oocyte development. The failure to identify the Müllerian duct in either sex between 11.5 and 12.5 dpc suggested that Wnt-4 regulates morphogenesis of this duct from the coelomic epithelium. Once the duct is formed, a second Wnt-member, Wnt-7a, regulates sex-specific development of the Müllerian duct and its derivatives. Thus, there are two phases to Wnt participation in the process of reproductive organogenesis. In the ovary, ectopic activation of genes encoding enzymes in the testosterone biosynthetic pathway (whose gonadal expression is normally restricted to the testis) indicated that during normal development, ovary specific expression of Wnt-4 suppressed Leydig cell development. As Wnt-4 expression is lost in the testis in conjunction with male sex determination, Wnt-4 is negatively regulated by the male sex determining pathway.

Outside the gonad, Wnt-4 is also expressed in the adrenal cortex of both sexes consistent with a broader role for Wnt-4 in the regulation of steroidogenesis. Two nuclear factors, SF-1 and Dax-1 demonstrate a connection between sex specific differentiation in the gonad and regulation of adrenal gland development. The early loss of the female germ line indicated that Wnt-4 is involved in the post-meiotic maintenance of oocytes. Oocytes have been shown to grow and survive in the adrenal gland of both sexes where the oocytes are in association with Wnt-4 expressing cells. These observations indicate that Wnt-4 supports oocyte development in this or other ectopic locations (or in in vitro culture conditions) in which oocytes are exposed to or contacted with Wnt-4.

EXAMPLE 2

Sexually Dimorphic Development of the Mammalian Reproductive Tract Requires Wnt-7a A striking feature of mammalian development is the generation of sexually dimorphic reproductive tracts from the Müllerian and Wolffian ducts. The data described below demonstrate that male mice lacking the Wnt-7a signaling molecule fail to undergo Müllerian duct regression due to the absence of normal MIS receptor expression. Wnt-7a deficient females were infertile due to abnormal development of the oviduct and uterus, both Müllerian duct derivatives. Therefore, Wnt-7a signaling permits sexually dimorphic development of the Müllerian ducts.

Wnt-7a is a member of the Wnt family of secreted glycoproteins that function as cell signaling molecules in a variety of developmental contexts. Mice homozygous for a mutant Wnt-7a allele (Wnt-7a deficient mice) exhibit defects in limb patterning, but otherwise appear fully viable.

To study the role of Wnt-7a in reproductive organs, pregnancies resulting from mating Wnt-7a-deficient mice were examined. Wnt-7a associated sterility in female animals was evaluated as follows.

Generation of Wnt-7a Mutant Mice

A null allele of Wnt-7a was produced and mice carrying the mutant allele generated according to known methods (e.g, the method described in Parr et al., 1995, Nature 374:350–353). The mutant allele was made by inserting a neomycin resistance gene into the second exon of the Wnt-7a locus. Mice with the mutant allele produce a non-functional Wnt-7a polypeptide which is translated from a truncated Wnt-7a transcript. Genotyping of embryos and postnatal animals by Southern blots confirmed presence of the mutant allele.

Histology

Reproductive tracts were dissected in phosphate-buffered saline (PBS) and fixed in Bouin's fixative. After dehydration through an ethanol series, the specimens were embedded in paraffin and sectioned at 7 mm. The sectioned slides were stained with hematoxylin and eosin and photographed on a Leitz DM RB microscope using Ektachrome 64T film. Comparative photographs of wild type and mutant siblings are at the same magnification.

In situ Hybridization

In situ hybridizations to 6 mm paraffin sections were performed using standard methods. Photographs were taken on a Leitz Aristoplan microscope using Fujichrome Velvia film and blue and red filters to give a double exposure image.

Whole Mount Photography

Reproductive tracts from neonatal or adult mice were dissected in PBS. Whole mount photographs of the reproductive tracts were taken in PBS on an Olympus SZH1O camera using Ektachrome 64T film.

Computer Graphics

A Kodak RFS 2035 slide scanner was used to scan 35 mm slides into Adobe Photoshop 3.0 on a Power Macintosh 8100.

Wnt-7a and Development of Reproductive Organs

The reproductive tracts of postnatal mice were dissected. When Wnt-7a homozygous females were compared to wild type or heterozygous littermates as either neonates or adults, their Müllerian duct derivatives were found to be improperly differentiated. At the neonatal stage, Müllerian ducts were present but there were no signs of coiled oviducts in Wnt-7a homozygous females. In addition, the uterine wall was thinner and notably less muscular than that of the wild type. Adult Wnt-7a −/− females lacked visibly coiled oviducts, and while their uteri were larger than at neonatal stages, they remained smaller than those of wild type siblings. Histological sections through the anterior region of the reproductive tract of Wnt-7a mutant females reveal a fimbriated, ciliated epithelium typical of the proximal oviduct. More posterior sections revealed a less elaborately folded mucosa made up of a simple columnar epithelium, with a prominent layer of circularly arranged smooth muscle beneath. Although the mucosa was less well developed than wild type, this region resembled the isthmic region of the oviduct. These data indicate that regional differentiation occurred along the oviduct, but normal elongation of this highly coiled ductal system did not occur.

At the uterine level, the radial diameter was less than half that of wild type siblings. The most prominent feature was a virtual absence of uterine glands, which are derived from the uterine epithelium, and a reduction in the mesenchymally derived uterine stroma so that the transverse and circular muscles, which were present but reduced, came to lie closer to the endometrial epithelium. Thus, in the absence of Wnt-7a, both epithelial and mesenchymal differentiation were disrupted in the uterus. Significantly, at both neonatal and adult stages, the ovaries, which are not derived from the Müllerian duct, underwent normal follicular growth, ovulation and cycling in the adult. Thus, the normal hormonal regulation of reproductive development does not appear to be altered in Wnt-7a mutants, indicating that the observed phenotype was unlikely to reflect an absence of the steroid hormones that coordinate uterine and ovarian development. As live born offspring were obtained from ovaries transplanted to recipient wild-type females, the evidence indicates that a failure intrinsic to the Müllerian duct led to female infertility.

Persistent Müllerian ducts were seen in Wnt-7a homozygous males throughout postnatal life. The non-regressed ducts appear as thin undifferentiated tubes that run alongside the epididymis and vas deferens from the testis to the urogenital sinus. The presence of a second duct appears to prevent the vas deferens from making a proper connection at its distal end, a condition also seen in MIS and MIS-receptor deficient mice, resulting in a block to sperm passage. Examination of the Müllerian ducts in adult males revealed a thin, poorly differentiated structure consisting of little more than a uniform cuboidal epithelium with a thin layer of muscle beneath, and no regional differentiation along its length. The testes and Wolffian duct derivatives of Wnt-7a mutant males appeared normal and mature sperm filled the vas deferens. Thus, Wnt-7a does not play a role in development of the male reproductive system, but is required for Müllerian duct regression. The persistent Müllerian duct prevents the exit of sperm leading to male sterility.

To determine how Wnt-7a regulates Müllerian duct development, Wnt-7a expression was examined in the embryonic urogenital system. Müllerian ducts arise from the coelomic epithelium in the mesonephric region of the mouse embryo under the influence of Wnt-4 between 11.5 and 12.5 dpc. Wnt-7a was found to be expressed along the length of the Müllerian duct epithelium of both sexes from 12.5 to 14.5 dpc, but was then lost from males following Müllerian duct regression. In the female, epithelial specific Wnt-7a expression continued in Müllerian duct derivatives throughout life consistent with a role for Wnt-7a signaling in both fetal and adult aspects of ductal development. The gene targeting strategy used to generate Wnt-7a deficient mice was insertion of a neomycin resistance gene into the second exon of the Wnt-7a locus. This construct generated a nonfunctional protein translated from a truncated Wnt-7a transcript. The truncated Wnt-7a transcripts were detected in Wnt-7a −/− mice during embryogenesis, and these transcripts served as useful markers for the Müllerian duct epithelium. At 14.5 dpc, Wnt-7a transcripts were still detected in the Müllerian duct epithelium of both sexes.

Thus, by this criterion, the epithelium was developing normally. These data indicated that epithelial-derived Wnt-7a signal functions by regulating gene expression in the adjacent mesenchyme.

To confirm this mechanism, expression of the MIS type II receptor in the mesenchyme was examined. Wild type males and females were found to express the receptor in mesenchymal cells surrounding the Müllerian duct at 14.5 dpc. In addition, males also expressed the receptor in Sertoli cells of the testis. However, expression was absent from the Müllerian duct mesenchyme in Wnt-7a mutant males and females, while expression in the testis was unaltered. These data indicate that Wnt-7a is required for regulation of MIS receptor expression in the periductal mesenchyme and subsequent regression of the Müllerian duct in males and that Wnt-7a acts as a signal from the epithelium to the surrounding mesenchyme during Müllerian duct development. The epithelial to mesenchymal signaling recalls the role of Wnt-7a in limb bud patterning, where it signals from the dorsal ectoderm to the underlying mesenchyme to regulate expression of Lmx-lb, thereby patterning the dorsal limb.

Estrogen and progesterone is important for development of the uterus after birth. Their target is also the stromal mesenchyme. Whereas progesterone only appears to function in pregnancy, estrogen receptor mutants have hypoplastic development of the uterine epithelium, stroma and muscle and a marked loss of uterine glands in the adult female. The loss of Wnt-7a was found to lead to a more severe phenotype than the estrogen deficiency; however, the similarities suggested that Wnt-7a may also be required for mediating a stromal response to estrogen.

Although the persistence of the Müllerian duct in Wnt-7a mutant males was consistent with a loss of MIS signaling, mutants lacking either MIS or its receptor formed well developed oviducts and uteri in the male. In contrast, the persistent Müllerian duct in Wnt-7a −/− males was a simple, undifferentiated tube with no regional organization. These data indicated that, as in the female, Wnt-7a function is also necessary for further differentiation of the Müllerian duct and that Wnt-7a is not acting simply as an effector of MIS function in Müllerian duct regression, but plays a more extensive role in regulating morphogenesis of ductal derivatives. The results further indicate that Wnt-7a signaling lies near the top of a differentiation pathway required for Müllerian duct development in both sexes. After Wnt-4 initiates ductal formation, Wnt-7a functions as an epithelial to mesenchymal signal rendering the mesenchyme competent to respond to MIS signaling through the MIS receptor.

EXAMPLE 3

Wnt-derived contraceptive Agents

The ability of Wnt polypeptides to promote oocyte development is inhibited by Wnt antagonists. Wnt antagonists, e.g., inhibitors of Wnt-signalling in female reproductive organs, are administered to humans and other animals, e.g., dogs or cats, to inhibit oocyte development as a method of birth control. For contraceptive purposes, Wnt antagonists inhibit signalling by Wnt-1 class Wnt polypeptides (e.g., Wnt-1, 2, 3a, 4, 7a, or 7b, the amino acid sequences of which are known and provided below). Soluble fragments of these Wnt polypeptides having the ability to inhibit Wnt signalling, e.g., by blocking binding of a naturally-occurring Wnt polypeptide to its receptor, are useful as Wnt antagonists. Polypeptides with such inhibitory activity are identified using methods described below.

TABLE 1

Human Wnt-1 amino acid sequence

```
  1 MGLWALLPGW VSATLLIALA ALPAALAANS SGRWWGIVNV ASSTNLLTDS KSLQLVLEPS
 61 LQLLSRKQRR LIRQNPGILH SVSGGLQSAV RECKWQFRNR RWNCPTAPGP HLFGKIVNRG
121 CRETAFIFAI TSAGVTHSVA RSCSEGSIES CTCDYRRRGP GGPDWHWGGC SDNIDFGRLF
181 GREFVDSGEK GRDLRFLMNL HNNEAGRTTV FSEMRQECKC HGMSGSCTVR TCWMRLPTLR
241 AVGDVLRDRF DGASRVLYGN RGSNRASRAE LLRLEPEDPA HKPPSPHDLV YFEKSPNFCT
301 YSGRLGTAGT AGRACNSSSP ALDGCELLCC GRGHRTRTQR VTERCNCTFH WCCHVSCRNC
361 THTRVLHECL (SEQ ID NO:3)
```

TABLE 2

Human Wnt-2 amino acid sequence

```
MNAPLGGIWLWLPLLLTWLTPEVNSSWWYMRATGGSSRVMCDNV
PGLVSSQRQLCHRHPDVMRAISQGVAEWTAECQHQFRQHRWNCNTLDRDHSLFGRVLL
RSSRESAFVYAISSAGVVFAITRACSQGEVKSCSCDPKKMGSAKDSKGIFDWGGCSDN
IDYGIKFARAFVDAKERKGKDARALMNLHNNRAGRKAVKRFLKQECKCHGVSGSCTLR
TCWLAMADFRKTGDYLWRKYNGAIQVVMNQDGTGFTVANERFKKPTKNDLVYFENSPD
YCIRDREAGSLGTAGRVCNLTSRGMDSCEVMCCGRGYDTSHVTRMTKCGCKFHWCCAV
RCQDCLEALDVHTCKAPKNADWTTAT (SEQ ID NO:4)
```

TABLE 10

Human Wnt-3a amino acid sequence

```
CKCHGLSGSC EVKTCWWSQP DFRAIGDFLK DKYDSASEMV
VEKHRESRGW VETLRPRYTY FKVPTERDLV YYEASPNFCE
PNPETGSFGT RDRTCNVSSH GIDGCDLLCC GRGHNARAER
RREKCRCVFH WCC (SEQ ID NO:5)
```

TABLE 4

Human Wnt-4 amino acid sequence

```
GVSGSCEVKT CWRAVPPFRQ VGHALKEKFD GATEVEPRRV GSSRALVPRN AQFKPHTDED
LVYLEPSPDF CEQDMRSGVL GTRGRTCNKT SKAIDGCELL CCGRGFHTAQ VELAERCSCK
(SEQ ID NO:6)
```

TABLE 5

Human Wnt-7a amino acid sequence

```
  1 MNRKALRCLG HLFLSLGMVC LRIGGFSSVV ALGATIICNK IPGLAPRQRA ICQSRPDAII
 61 VIGEGSQMGL DECQFQFRNG RWNCSALGER TVFGKELKVG SRDGAFTYAI IAAGVAHAIT
121 AACTHGNLSD CGCDKEKQGQ YHRDEGWKWG GCSADIRYGI GFAKVFVDAR EIKQNARTLM
181 NLHNNEAGRK ILEENMKLEC KCHGVSGSCT TKTCWTTLPQ FRELGYVLKD KYNEAVHVEP
```

TABLE 5-continued

Human Wnt-7a amino acid sequence

```
241 VRASRNKRPT FLKIKKPLSY RKPMDTDLVY IEKSPNYCEE DPVTGSVGTQ GRACNKTAPQ
301 ASGCDLMCCG RGYNTHQYAR VWQCNCKFHW CCYVKCNTCS ERTEMYTCK
(SEQ ID NO:7)
```

TABLE 6

Human Wnt-7b partial amino acid sequence

```
  1 GVSGSCTTKT CWTTLPKFRE VGHLLKEKYN AAVQVEVVRA SRLRQPTFLR IKQLRSYQKP
 61 METDLVYIEK SPNYCEEDAA TGSVGTQGRI CNRTSPGADG CDTMCCGRGY NTHQYTKVWQ
121 CNCK (SEQ ID NO:8)
```

Other Wnt antagonists include Wnt polypeptides of the Wnt-5a class, e.g., Wnt-5a.

TABLE 7

Human Wnt-5a amino acid sequence

```
  1 MAGSAMSSKF FLVALAIFFS FAQVVIEANS WWSLGMNNPV QMSEVYIIGA QPLCSQLAGL
 61 SQGQKKLCHL YQDHMQYIGE GAKTGIKECQ YQFRHRRWNC STVDNTSVFG RVMQIGSRET
121 AFTYAVSAAG VVNAMSRACR EGELSTCGCS RAARPKDLPR DWLWGGCGDN IDYGYRFAKE
181 FVDARERERI HAKGSYESAR ILMNLHNNEA GRRTVYNLAD VACKCHGVSG SCSLKTCWLQ
241 LADFRKVGDA LKEKYDSAAA MRLNSRGKLV QVNSRFNSPT TQDLVYIDPS PDYCVRNEST
301 GSLGTQGRLC NKTSEGMDGC ELMCCGRGYD QFKTVQTERC HCKFHWCCYV KCKKCTEIVD
361 QFVCK (SEQ ID NO:9)
```

Wnt antagonists also include compositions which inhibit other events in the Wnt signalling pathway, e.g., signal transduction by β-catenin. Thus, dominant negative mutants of β-catenin such are those which bind to upstream or downstream components of the signalling pathway but fail to transduce a signal as useful Wnt antagonists. For example, dominant negative mutants of β-catenin lack one or more armidillo-like repeats which participate in cadherin binding. For example, at least repeats 11–13 (amino acids 555–695 of SEQ ID NO:10) are deleted. Other mutants which fail to bind cadherin include those which lack amino acids 555–781 of SEQ ID NO:10, those which lack amino acids 424–781 of SEQ ID NO:10, and those which lack amino acids 1–422 of SEQ ID NO:10.

TABLE 8

Human β-catenin

MATQADLMELDMAMEPDRKAAVSHWQQQSYLDSGIHSGATTTAPSLSGKGNPEEEDVDTSQVLYEWEQGF

SQSFTQEQVADIDGQYAMTRAQRVRAAMFPETLDEGMQIPSTQFDAAHPTNVQRLAEPSQMLKHAVVNLI

NYQDDAELATRAIPELTKLLNDEDQVvvNKAAVVVHQLSKEEASRHAIMRSPQMVSAIVRTMQNTNDVET

ARCTAGTLHNLSHHREGLLAIFKSGGIPALVKMLGSPVDSVLFYAITTLHNLLLHQEGAKMAVRLAGGLQ

KMVALLNKTNVKFLAITTDCLQILAYGNQESKLIILASGGPQALVNIMRTYTYEKLLWTTSRVLKVLSVC

SSNKPAIVEAGGMQALGLHLTDPSQRLVQNCLWTLRNLSDAATKQEGMEGLLGTLVQLLGSDDINVVTCA

AGILSNLTCNNYKNKMMVCQVGGIEALVRTVLRAGDREDITEPAICALRHLTSRHQEAEMAQNAVHLHYG

TABLE 8-continued

Human β-catenin

LPVVVKLLHPPSHWPLIKATVGLIRNLALCPAHHAPLREQGAIPRLVQLLVRAHQDTQRRTSMGGTQQQF

VEGVRMEEIVEGCTGALHILARDVHNRIVIRGLNTIPLFVQLLYSPIENIQRVAAGVLCELAQDKEAAEA

IEAEGATAPLTELLHSRNEGVATYAAAVLFRMSEDKPQDYKKRLSVELTSSLFRTEPMAWNETADLGLDI

GAQGEPLGYRQDDPSYRSFHSGGYGQDALGMDPMMEHEMGGHHPGADYPVDGLPDLGHAQDLMDGLPPGD

SNQLAWFDTDL (SEQ ID NO:10)

---

Signal transduction by β-catenin is mediated by binding to the cytoplasmic domain of a cadherin, e.g., N-cadherin, a glycoprotein which mediates cell adhesion. Accordingly, dominant negative mutants of N-cadherin which inhibit Wnt-1 class signals can also be used as Wnt antagonists for inhibition of oocyte development. For example, a dominant negative cadherin mutant lacks at least 20 amino acids of the cytoplasmic domain and up to the entire the cytoplasmic domain of N-cadherin. Preferably, a dominant negative mutant lacks the cytoplasmic catenin binding domain of N-cadherin. Mutants are terminally deleted or contain an internal deletion. Other dominant negative mutants lack extracellular cysteines, e.g., the cysteine residues were replaced with another amino acid such as serine, or lack a portion, e.g., at least 50 amino acids, or all of the extracellular domain. Dominant negative N-cadherin mutants are known in the art and described in Torres et al., 1996, J. Cell Biol. 133:1123–1137 and Kintner et al., 1992, Cell 69:225–236.

The extracellular domain of human N-cadherin spans amino acids 160–724, and the cytoplasmic domain spans amino acids 747–906.

Wnt receptors such as Frizzled receptor proteins or fragments thereof, e.g., soluble fragments of Frizzled polypeptides or Frizzled-like polypeptides containing a cysteine-rich domain, are also useful Wnt antagonists for inhibition of oocyte development. Other Wnt antagonists are known in the art. For example, Fritz is a secreted protein which is structurally related to the extracellular domain of Frizzled and interferes with Wnt association with Frizzled receptors (Mayr et al., 1997, Mech. Dev. 63:109–125). Frzb-1 is a secreted antagonist of Wnt signalling (Leyns et al., 1997, Cell 88:747–756). Secreted Frizzled related proteins (sFRP) are a family of secreted proteins the amino acid sequence of which contains a conserved cysteine-rich domain (Rattner et al., 1997, Proc. Natl. Acad. Sci. USA 94:2859–2863 and Finch et al., 1997, Proc. Natl. Acad. Sci. USA 94:6770–7775). Secreted apoptosis-related proteins (SARPs) contain a conserved cysteine-rich domain and modify intracellular levels of β-catenin, thereby disrupting Wnt-1 class signal

TABLE 9

Human N-cadherin

|   |   |   |   |   |   |   |
|---|---|---|---|---|---|---|
| 1 | MCRIAGALRT | LLPLLLALLQ | ASVEASGEIA | LCKTGFPEDV | YSAVLSKDVH | EGQPLLNVKF |
| 61 | SNCNGKRKVQ | YESSEPADFK | VDEDGMVYAV | RSFPLSSEHA | KFLIYAQDKE | TQEKWQVAVK |
| 121 | LSLKPTLTEE | SVKESAEVEE | IVFPRQFSKH | SGHLQRQKRD | WVIPPINLPE | NSRGPFPQEL |
| 181 | VRIRSDRDKN | LSLRYSVTGP | GADQPPTGIF | IINPISGQLS | VTKPLDREQI | ARFHLRAHAV |
| 241 | DINGNQVENP | IDIVINVIDM | NDNRPEFLHQ | VWNGTVPEGS | KPGTYVMTVT | AIDADDPNAL |
| 301 | NGMLRYRIVS | QAPSTPSPNM | FTINNETGDI | ITVAAGLDRE | KVQQYTLIIQ | ATDMEGNPTY |
| 361 | GLSNTATAVI | TVTDVNDNPP | EFTAMTFYGE | VPENRVDIIV | ANLTVTDKDQ | PHTPAWNAVY |
| 421 | RISGGDPTGR | FAIQTDPNSN | DGLVTVVKPI | DFETNRMFVL | TVAAENQVPL | AKGIQHPPQS |
| 481 | TATVSVTVID | VNENPYFAPN | PKIIRQEEGL | HAGTMLTTFT | AQDPDRYMQQ | NIRYTKLSDP |
| 541 | ANWLKIDPVN | GQITTIAVLD | RESPNVKNNI | YNATFLASDN | GIPPMSGTGT | LQIYLLDIND |
| 601 | NAPQVLPQEA | ETCETPDPNS | INITALDYDI | DPNAGPFAFD | LPLSPVTIKR | NWTITRLNGD |
| 661 | FAQLNLKIKF | LEAGIYEVPI | IITDSGNPPK | SNISILRVKV | CQCDSNGDCT | DVDRIVGAGL |
| 721 | GTGAIIAILL | CIIILLILVL | MFVVWMKRRD | KERQAKQLLI | DPEDDVRDNI | LKYDEEGGGE |
| 781 | EDQDYDLSQL | QQPDTVEPDA | IKPVGIRRMD | ERPIHAEPQY | PVRSAAPHPG | DIGDFINEGL |
| 841 | KAADNDPTAP | PYDSLLVFDY | EGSGSTAGSL | SSLNSSSSGG | EQDYDYLNDW | GPRFKKLADM |
| 901 | YGGGDD (SEQ ID NO:11) | | | | | | transduction via the Wnt-frizzled pathway (Melkonyan et al., 1997, Proc. Natl. Acad. Sci. USA 9:13636–13641).

Oocytes are contacted with a Wnt antagonist which inhibits Wnt binding to its cognate receptor, e.g., the Frizzled receptor protein. The Frizzled receptor protein contains a cysteine-rich domain which is involved in Wnt binding. A peptide containing a cysteine-rich domain, e.g., a cysteine-rich domain of a Frizzled receptor, Frizzled-like protein, or tyrosine kinase receptor, is used to inhibit association of a Wnt polypeptide with a Frizzled receptor. Such peptides contain the consensus amino sequence of SEQ ID NO:1 or 2, where X is any amino acid.

All Frizzled proteins share the following structural similarities: a signal sequence at the amino terminus, a conserved region of approximately 120 amino acids in the extracellular domain containing a motif of 10 invariantly spaced cysteines (cysteine-rich domain), a seven-pass transmembrane region, and a cytoplasmic domain with little homology among family members. Examples of Frizzled and receptor tyrosine kinases peptides with cysteine-rich domains are known in the art, e.g., those described in Saldanha et al., 1998, Protein Science 7:1632–1635; Xu et al., 1998, Curr. Biol. 8:R405–6; Masiakowski et al., 1998, Curr. Biol. 8:R407; and Saldahha et al., 1998, Protein Science 7:1632–1635.

To render the therapeutic peptides less susceptible to cleavage by peptidases, the peptide bonds of a peptide may be replaced with an alternative type of covalent bond (a "peptide mimetic"). Where proteolytic degradation of the peptides following injection into the subject is a problem, replacement of a particularly sensitive peptide bond with a noncleavable peptide mimetic will make the resulting peptide more stable and thus, more useful as a therapeutic. Such mimetics, and methods of incorporating them into polypeptides, are well known in the art. Similarly, the replacement of an L-amino acid residue with a D-amino acid is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell. This modification may be especially useful in the delivery of peptides into cells, the delivery of peptides to inhibit intracellular Wnt-mediated signal transduction. Liposomal delivery is also favored for intracellular delivery of compounds.

Wnt antagonists are administered to animals, e.g., a human patient, in pharmaceutically acceptable carriers (e.g., physiological saline), which are selected on the basis of the mode and route of administration and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF.

A therapeutically effective amount is an amount which is capable of producing medically desirable result, e.g., contraception, in a treated animal. As is well known in the medical arts, dosage for any one patient depends upon many factors, including the patient's size, body surface area, age, the particular compound to be administered, sex, time and route of administration, general health, and other drugs being administered concurrently.

An antibody which inhibits Wnt-signalling can also be used as a Wnt antagonist for contraceptive purposes. For administration to human patients, antibodies, e.g., Wnt-specific monoclonal antibodies, can be humanized by methods known in the art. Antibodies with a desired binding specificity can be commercially humanized (Scotgene, Scotland; Oxford Molecular, Palo Alto, Calif.).

Wnt antagonists are administered to a patient by any appropriate method, e.g., locally such as a coating on an intrauterine device or as an intraperitoneal implant, or systemically, for contraception. For example, Wnt antagonists are administered orally, using dosing regimens similar to those used for steroid-based oral contraceptives. For control of wildlife species or urban control of nuisance animals, the compositions may be administered food or bait. Transmucosal, transdermal, or surgical administration such as implantation of Wnt antagonists, e.g. encapsulated in hard or soft tubing or incorporated into a solid or semi-solid biologically compatible and resorbable matrix, can also be used. Appropriate transdermal delivery systems and subdermally implantatable contraceptive delivery devices are known in the art, e.g., U.S. Pat. No. 5,762,956 and U.S. Pat. No. 5,756,115, respectively. An antagonist can also be administered rectally, e.g., in the form of a suppository capsule. Therapeutic doses are determined specifically for each compound, most being administered within the range of 0.001 to 100.0 mg/kg body weight, or within a range that is clinically determined to be appropriate by one skilled in the art. A Wnt antagonist may be administered daily throughout the menstrual cycle. Alternatively, the composition is administered congruent with ovulation, e.g., from a time 1–3 days before ovulation for a period of 5–6 days or to approximately the end of the menstrual cycle.

EXAMPLE 4

Wnt-specific Antibodies

Wnt-specific antibodies, e.g., antibodies that bind to Wnt-4 or Wnt-7a and thereby inhibit Wnt-signalling, are produced using standard methodologies for raising polyclonal antisera and making monoclonal antibody-producing hybridoma cell lines (see Coligan et al., eds., *Current Protocols in Immunology*, 1992, Greene Publishing Associates and Wiley-Interscience). To generate monoclonal antibodies, a mouse is immunized with a Wnt polypeptide, e.g., a peptide having at least 10 amino acids of the amino acid sequence of any one of SEQ ID NO:3-8, antibody-secreting B cells isolated from the mouse, and the B cells immortalized with a non-secretory myeloma cell fusion partner. Hybridomas are then screened for production of a Wnt-specific antibody and cloned to obtain a homogenous cell population which produces a monoclonal antibody.

Antibodies are further screened for the ability to block Wnt-signalling. For example, antibodies found to bind to a Wnt polypeptide are then incubated with the Wnt polypeptide and a receptor with which it binds. The Wnt peptide may have the amino acid sequence of a full-length naturally-occurring Wnt polypeptide or it may be a shorter peptide containing the amino acid sequence of a Wnt domain know to participate in receptor binding; the receptor peptide may have the amino acid sequence of a full-length naturally-occurring Wnt receptor, e.g., the Frizzled receptor, or it may be a shorter peptide containing a binding domain, e.g., a cysteine-rich domain. A decrease in Wnt/receptor binding in the presence of an antibody compared to that in the absence of the antibody indicates that the antibody inhibits binding of the Wnt polypeptide to its receptor and thereby inhibits Wnt signalling. The ability of such antibodies to inhibit oocyte development is then confirmed in vitro and in animals using the screening methods described herein.

EXAMPLE 5

Identification and Use of Compositions Which Inhibit Wnt Signalling

Wnt antagonists can be generated, for example, by combinatorial mutagenesis techniques well known in the art (See, for example, Ladner et al. PCT publication WO 90/02909; Garrard et al., PCT publication WO 92/09690; Marks et al., 1992, J. Biol. Chem. 267:16007–16010; Griffiths et al., 1993, EMBO J 12:725–734; Clackson et al., 1991, Nature 352:624–628; and Barbas et al., 1992, PNAS 89:4457–4461). Peptidomimetics of such antagonists or other small molecules, such as may be identified in the assays set out below, can also be used to antagonize Wnt signalling. For example, the antagonists block signal transduction by the Frizzled receptor. Such agents include dominant negative mutants of Wnt pathway proteins, e.g., a dominant negative mutant of N-cadherin or β-catenin. Other agents which inhibit the Wnt receptor second messenger pathways downstream of the Frizzled receptor can also be used to inhibit Wnt-mediated oocyte development.

Primary screening assays are performed in cell-free systems, e.g., using purified or semi-purified proteins such as Wnt-4 or Wnt-7a and the receptors to which they bind. A candidate compound is contacted with a mixture containing a Frizzled receptor or a cell expressing the Frizzled receptor and a Wnt protein, e.g., Wnt-4 or Wnt-7a, under conditions in which it is ordinarily capable of binding the Wnt protein. To the mixture is then added a candidate compound. A decrease in the number of receptor/Wnt complexes in the presence of a candidate compound compared to the number in the absence of the compound indicates that the compound inhibits the association between a receptor protein and the Wnt polypeptide and thereby inhibits Wnt-signalling involved in oocyte development. Wnt antagonists are further evaluated in vitro for the ability to inhibit oocyte viability and development, e.g., progression from an immature state to a mature state, as described below. Antagonists which inhibit progression of oocytes from an immature to a mature state are useful as contraceptive agents.

Compositions are evaluated in vitro as follows. Oocytes are harvested from animals and cultured in tissue culture medium in the presence and absence of a candidate compound. A decrease in the number and/or viability of oocytes (or in the number of mature oocytes) in a culture sample in the presence of a candidate Wnt antagonist compared to one cultured in the absence of a Wnt antagonist indicates that the composition inhibits oocyte viability and/or development.

Screening of compounds for the ability to inhibit oocyte development is carried out in vivo by administering candidate antagonists of Wnt signalling, e.g., a dominant negative mutant of N-cadherin or β-catenin, to normal female animals, e.g., mice, and determining whether oocyte development is impaired compared to animals not receiving the composition. Following a course of administration of a Wnt antagonist, the mice are evaluated as described above, e.g., by examining the ovaries for depletion in the number of oocytes or decreased viability of oocytes.

EXAMPLE 6

Contraceptive Vaccine

A Wnt polypeptide containing an epitope which binds to a Wnt-specific antibody, e.g., an antibody that inhibits oocyte development, is administered to an animal to elicit antibodies. Such peptides are identified by standard methods of epitope mapping using Wnt-specific antibodies that inhibit Wnt signalling, e.g., those described in Example 4. For example, a polypeptide containing at least 10, preferably at least 20, more preferably at least 30, more preferably at least 50, amino acids of any one of SEQ ID NO:3–8. The polypeptides are administered as a vaccine for immunological control of fertility in female animals as described in U.S. Patent No. 3,992,520.

EXAMPLE 7

Use of Wnt Polypeptides to Promote Oocyte Development and Viability

Wnt polypeptides, e.g., Wnt-1, Wnt-2, Wnt-3a, Wnt-4, Wnt-7a, or Wnt-7b, are used as media supplements for culturing oocytes for the purpose enhancing viability of freshly isolated or cryopreserved oocytes and for promoting development, e.g., maturation, of oocytes in vitro or in vivo. For example, Wnt-supplemented media preparations are used to increase the fertilization potential of oocytes prior to contacting the oocytes with sperm cells in in vitro fertilization (IVF) procedures.

Any standard oocyte compatible tissue culture medium, e.g., Ham's Flo medium, is supplemented. Culture media suitable for oocyte culture are described in Wood and Trounson, eds., 1989, in Clinical in vitro Fertilization, 2nd ed. (London, Springer-Verlag). Wnt polypeptides are added to the medium at a concentration of at least 0.01 ng/ml. In preferred embodiments, the concentration is at least 0.1 ng/ml, in the range of 1 ng/ml to 100 mg/ml, and up to a concentration of about 10 mg/ml of tissue culture medium. Oocytes are cultured from at least one hour to up to several days, e.g., two days prior to use in IVF procedures.

Oocytes are obtained from donor females either during a natural cycle or after administration of a stimulating agent, e.g., a fertility enhancer such as clomiphene citrate, follicle stimulating hormone (FSH), a mixture of FSH and luteinizing hormone (LH), and/or human chorionic gonadotropins. An oocyte is retrieved from a follicle of an ovary using standard methods, e.g., transvaginal ultrasonically guided follicular aspiration. Oocytes may be retrieved from stimulated or unstimulated follicles. Even those retrieved from stimulated follicles may be mature or immature. Immature oocytes are those that are viable but incapable of fertilization without additional stimulation or maturation, whereas mature oocytes are capable of being fertilized upon being contacted with a sperm cell. Mature oocytes are distinguished from immature oocytes using standard criteria. For example, oocytes are visually assessed microscopically; mature oocytes have an expanded granulosa cell layer, no germinal vesicle and a single polar body while immature oocyes have two or more layers of surrounding condensed granulosa cells, a germinal vesicle, and no polar body.

Oocytes which have been cryopreserved using standard media preparations supplements with a cryoprotectant such as glycerol, propanediol, or dimethylsulfoxide, are thawed using standard protocols. Oocytes are contacted with a Wnt polypeptide during and/or after the thawing process to enhance cell viability and/or to promote maturation.

Other embodiments are within the following claims.

What is claimed is:

1. A method of promoting maturation of an immature oocyte comprising contacting said oocyte with a substantially pure preparation of a Wnt polypeptide, wherein said Wnt polypeptide comprises the amino acid sequence of SEQ ID NO:6.

2. A method of enhancing viability of an oocyte in vitro comprising contacting said oocyte with a Wnt polypeptide, wherein said Wnt polypeptide comprises the amino acid sequence of SEQ ID NO:6.

3. The method of claim 2, wherein said oocyte is cryopreserved and said contacting step occurs during thawing of said cryopreserved oocyte.

* * * * *